(12) United States Patent
Utama et al.

(10) Patent No.: US 10,316,314 B2
(45) Date of Patent: Jun. 11, 2019

(54) NUCLEIC ACID EXTRACTION METHOD

(71) Applicant: Delta Electronics Int'l (Singapore) Pte Ltd, Singapore (SG)

(72) Inventors: Revata Utama, Singapore (SG); Yong Zhang, Singapore (SG); Song Bin Huang, Singapore (SG); Wang Chu Chen, Singapore (SG)

(73) Assignee: DELTA ELECTRONICS INT'L (SINGAPORE) PTE LTD, Singapore (SG)

( * ) Notice: Subject to any disclaimer, the term of this patent is extended or adjusted under 35 U.S.C. 154(b) by 258 days.

(21) Appl. No.: 14/831,164

(22) Filed: Aug. 20, 2015

(65) Prior Publication Data

US 2017/0015992 A1  Jan. 19, 2017

(30) Foreign Application Priority Data

Jul. 15, 2015  (SG) ............................ 10201505563X

(51) Int. Cl.
*C12N 15/10* (2006.01)

(52) U.S. Cl.
CPC ................................ *C12N 15/1006* (2013.01)

(58) Field of Classification Search
CPC .......... C12N 15/1006; C12Q 2527/101; C12Q 2527/119
USPC ................................... 536/25, 410
See application file for complete search history.

(56) References Cited

U.S. PATENT DOCUMENTS

| | | | | |
|---|---|---|---|---|
| 6,120,985 A | * | 9/2000 | Laugharn, Jr. ........ | B01L 3/5027 435/1.3 |
| 2009/0215124 A1 | * | 8/2009 | Cao .................... | C12N 15/1006 435/91.2 |
| 2011/0081363 A1 | * | 4/2011 | Whitney ................. | A01N 1/00 424/184.1 |

FOREIGN PATENT DOCUMENTS

| | | |
|---|---|---|
| CN | 1882688 A | 12/2006 |
| CN | 102115711 A | 7/2011 |
| TW | 201425325 A | 7/2014 |
| WO | 02055727 A2 | 7/2002 |

OTHER PUBLICATIONS

Hagan et al, Anal. Chem. 2009, 81, 5249-5256.*
Cao, Weidong et al., "Chitosan as a Polymer for pH-Induced DNA Capture in a Totally Aqueous System," Anal. Chem., 2006, 78, 7222-7228.
Kendall, Eric L. et al., "A chitosan coated monolith for nucleic acid capture in a thermoplastic microfluidic chip," Biomicrofluidics 8, 044109 (2014).
Hagan et al., "Chitosan-Coated Silica as a Solid Phase for RNA Purification in a Microfluidic Device", Anal. Chem. vol. 81, No. 13, Jul. 1, 2009, 5249-5256.

* cited by examiner

*Primary Examiner* — Ganapathy Krishnan
(74) *Attorney, Agent, or Firm* — Kirton & McConkie; Evan R. Witt

(57) ABSTRACT

A nucleic acid extraction method includes the following steps. Firstly, a mixture of a sample and a lysis buffer is provided. The pH of the lysis buffer is lower than 7. Then, the mixture of the sample and the lysis buffer is transferred to a nucleic acid catching chamber containing chitosan coating material, so that nucleic acid of the sample is bound to the chitosan coating material. Then, the chitosan coating material is washed with at least one wash buffer, thereby removing residual protein and cell debris. Then, the chitosan coating material is eluted with an elution buffer while heating the chitosan coating material, so that the nucleic acid is separated from the chitosan coating material. The pH of the elution buffer is higher than 7.

10 Claims, 8 Drawing Sheets

| No. | Name | Total DNA (ng) | | |
|---|---|---|---|---|
| | | Run 1 | Run 2 | Run 3 |
| 1 | Original DNA | 3000 | 3240 | 3120 |
| 2 | Eluted DNA | 1224 | 1305 | 1207.5 |

| | % Recovery | 260/280 Value | 260/230 Value |
|---|---|---|---|
| Run 1 | 40.80% | 2.13 | 1.77 |
| Run 2 | 40.28% | 1.87 | 2.04 |
| Run 3 | 38.70% | 2.03 | 2.88 |

FIG. 6A

NUCLEIC ACID EXTRACTION METHOD

FIELD OF THE INVENTION

The present invention relates to a nucleic acid extraction method, and more particularly to a nucleic acid extraction method using a chitosan coating material.

BACKGROUND OF THE INVENTION

With advances in technology and transportation convenience, the propagation speeds of infectious diseases (e.g., SARS, avian flu, dengue fever and other diseases) are accelerated and become the challenges in today's world. Consequently, the medical laboratory scientists make efforts in providing an effective prevention strategy for rapidly detecting and confirming the suspected cases and early isolating or confirming the therapeutic treatment. In other words, a "real-time and in-situ detecting means" is an important issue to study infectious diseases.

Nowadays, the rapid screening immunology is widely used. Although the rapid screening immunology is able to conduct a preliminary screening within 30 minutes, its accuracy is only 30%~60%. Moreover, since the rapid screening immunology is only suitable for detecting a small number of infectious diseases, the applications thereof are limited. A molecular detection method can provide high accuracy detection and analysis. However, since many large expensive machines are needed and complicated procedures are operated by professional persons, the molecular detection method can be used in a small number of large-scale research and development centers and clinical analysis laboratories.

"Chip laboratory" is a novel concept proposed in recent years. In the chip laboratory, different miniature detection devices are integrated into the same platform so as to achieve the purposes of point of care (POC) and in vitro diagnostics (IVD). Its essence is to construct a medical detecting platform with "small volume", "high accuracy" and "real-time diagnostics".

The conventional method of extracting nucleic acid usually uses chaotropic salt such as guanidium hydrochloride (GuHCl) to bind DNA onto a silica membrane of a spin column, and inhibitors such as GuHCl, ethanol and isopropanol that influence the subsequent DNA analysis are washed away by high speed centrifugation. However, the inhibitors in the chip microfluidic system result in many problems. For example, the PCR reaction is adversely affected. Another method for extracting nucleic acid uses a chitosan coating material. However, the chitosan coating material of the conventional method is only able to extract at most 150 ng of DNA, and the recovery is usually unsatisfied.

Therefore, there is a need of providing an improved nucleic acid extraction method in order to overcome the above drawbacks.

SUMMARY OF THE INVENTION

An object of the present invention provides a nucleic acid extraction method with enhanced recovery and without using the inhibitory chemicals such as guanidium hydrochloride, ethanol and isopropanol.

Another object of the present invention provides a nucleic acid extraction method that can be integrated into a portable and automatic nucleic acid detection platform. Consequently, the nucleic acid extraction method is advantageous of establishing a portable biochip for automatically extracting and purifying DNA of the sample to meet the requirements of the subsequent DNA amplification and real-time diagnostics.

In accordance with an aspect of the present invention, there is provided a nucleic acid extraction method. Firstly, in a step (a), a mixture of a sample and a lysis buffer is provided. The pH of the lysis buffer is lower than 7. In a step (b), the mixture of the sample and the lysis buffer is transferred to a nucleic acid catching chamber containing a chitosan coating material, so that nucleic acid of the sample is bound to the chitosan coating material. In a step (c), the chitosan coating material is washed with at least one wash buffer, thereby removing residual protein and cell debris. In a step (d), the chitosan coating material is eluted with an elution buffer while heating the chitosan coating material, so that the nucleic acid is separated from the chitosan coating material. The pH of the elution buffer is higher than 7.

In an embodiment, the step (c) includes a step (c1) of washing the chitosan coating material with a first wash buffer and a step (c2) of washing the chitosan coating material with a second wash buffer. The pH of the first wash buffer is lower than 7. The pH of the second wash buffer is higher than 7.

In an embodiment, the pH of the first wash buffer is in a range between 4 and 7, and the pH of the second wash buffer is in a range between 7 and 11.

In an embodiment, the first wash buffer includes tris (hydroxymethyl)aminomethane (Tris), bis(2-hydroxyethyl) amino tris(hydroxymethyl)methane (BIS-TRIS), 1,3-bis(tris (hydroxymethyl) methylamino) propane (Bis-Tris Propane) and 3-(N-morpholino)propanesulfonic acid (MOPS).

In an embodiment, the second wash buffer includes 2-amino-2-methyl-1-propanol (AMP), tris(hydroxymethyl) aminomethane (Tris), N,N,-bis-(2-Hydroxyethyl) glycine (BICINE) and 4-(2-hydroxyethyl)-1-piperazineethanesulfonic acid (HEPES).

In an embodiment, the step (c1) is performed twice sequentially.

In an embodiment, the lysis buffer includes tris(hydroxymethyl)aminomethane (Tris), bis(2-hydroxyethyl) amino tris(hydroxymethyl)methane (BIS-TRIS), 1,3-bis(tris (hydroxymethyl) methylamino) propane (Bis-Tris Propane) and 3-(N-morpholino)propanesulfonic acid (MOPS).

In an embodiment, the pH of the lysis buffer is in a range between 4 and 7.

In an embodiment, the lysis buffer contains a cell lysis detergent.

In an embodiment, the pH of the elution buffer is in a range between 7 and 11.

In an embodiment, the elution buffer includes 2-amino-2-methyl-1-propanol (AMP), tris(hydroxymethyl)aminomethane (Tris), N,N,-bis-(2-Hydroxyethyl) glycine (BICINE) and 4-(2-hydroxyethyl)-1-piperazineethanesulfonic acid (HEPES).

In an embodiment, the chitosan coating material in the step (d) are heated to 35~65° C.

In an embodiment, a heater plate is disposed under the nucleic acid catching chamber for heating the chitosan coating material.

In an embodiment, the nucleic acid extraction method is implemented in a biochip cartridge.

In an embodiment, the biochip cartridge includes a sample chamber, at least one wash buffer chamber, an elution buffer chamber, the nucleic acid catching chamber and a waste chamber.

The above contents of the present invention will become more readily apparent to those ordinarily skilled in the art after reviewing the following detailed description and accompanying drawings, in which:

BRIEF DESCRIPTION OF THE DRAWINGS

FIGS. 6A and 6B illustrate the DNA extraction results of the rat genomic DNA by the nucleic acid extraction method of the present invention.

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

The present invention provides a nucleic acid extraction method. In accordance with the present invention, DNA is bound to a chitosan coating material in an acidic environment, and eluted in a basic environment, so that the DNA is extracted. Since the inhibitory chemicals (e.g., guanidium hydrochloride, ethanol and isopropanol) are not contained in the buffer system, the yield of the high purity nucleic acid is increased and the result of the subsequent DNA analysis is not adversely affected.

In particular, the nucleic acid is bound to the chitosan in the presence of a lysis buffer with high ionic strength at low pH. The high ionic strength of the buffer system helps protonation of the chitosan by transferring protons to the glucosamine chain of the chitosan. Consequently, the chitosan brings positive charges, and under this circumstance, the ability of chitosan to bind the nucleic acid with negative charges will be increased. That is, the nucleic acid can be easily bound to the chitosan. In contrast to the lysis buffer, an elution buffer has low ionic strength at high pH. The elution buffer is used to eliminate the protonation of the chitosan. Once the chitosan becomes neutral, the nucleic acid is released to the elution buffer.

Figure 1:
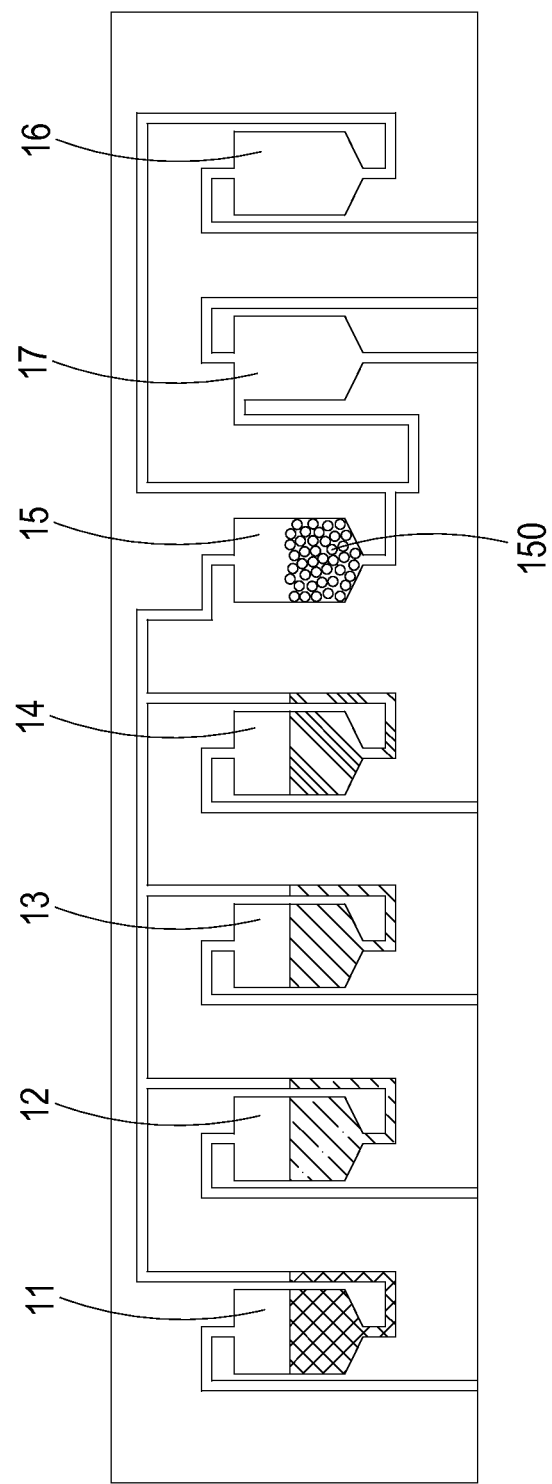
FIG. 1 is a schematic fluidic flow diagram illustrating a method for extracting nucleic acid according to an embodiment of the present invention.

FIG. 1 is a schematic fluidic flow diagram illustrating a method for extracting nucleic acid according to an embodiment of the present invention. The nucleic acid extraction method is implemented in a biochip cartridge. As shown in FIG. 1, the biochip cartridge comprises a sample chamber 11, a first wash buffer chamber 12, a second wash buffer chamber 13, an elution buffer chamber 14, a nucleic acid catching chamber 15, a waste chamber 16 and a nucleic acid collector 17.

A mixture of a sample and a lysis buffer is stored in the sample chamber 11. For example, the sample is blood, urine, sweat, saliva or a specimen collected by a cotton swab. The volume of the sample is about 20-50 μl. The pH of the lysis buffer is lower than 7 (e.g. 4~7). For example, the lysis buffer includes but not limited to tris(hydroxymethyl)aminomethane (Tris), bis(2-hydroxyethyl)amino tris(hydroxymethyl)methane (BIS-TRIS), 1,3-bis(tris(hydroxymethyl)methylamino) propane (Bis-Tris Propane) and 3-(N-morpholino)propanesulfonic acid (MOPS). The lysis buffer may contain a cell lysis detergent such as Tween-20, Tween-80, CHAPS, NP-40, Igepal or CA-630. Optionally, the lysis buffer contains salts such as NaCl, KCl, NaF, $CaCl_2$ and/or $MgCl_2$. In an embodiment, the pH of the lysis buffer is 4~6, preferably 5. Moreover, the volume of the lysis buffer is about 150 μl, but is not limited thereto.

A first wash buffer is stored in the first wash buffer chamber 12. The pH of the first wash buffer is lower than 7 (e.g. 4~7). For example, the first wash buffer includes but not limited to tris(hydroxymethyl)aminomethane (Tris), bis(2-hydroxyethyl)amino tris(hydroxymethyl)methane (BIS-TRIS), 1,3-bis(tris(hydroxymethyl)methylamino) propane (Bis-Tris Propane) and 3-(N-morpholino)propanesulfonic acid (MOPS). The pH of the first wash buffer is adjusted by using HCl. In an embodiment, the pH of the first wash buffer is 4~6, preferably 5. Moreover, the volume of the first wash buffer is about 380 μl, but is not limited thereto.

A second wash buffer is stored in the second wash buffer chamber 13. The pH of the second wash buffer is higher than 7 (e.g. 7~11). The second wash buffer includes but not limited to 2-amino-2-methyl-1-propanol (AMP), tris(hydroxymethyl)aminomethane (Tris), N,N,-bis-(2-Hydroxyethyl) glycine (BICINE) and 4-(2-hydroxyethyl)-1-piperazineethanesulfonic acid (HEPES). The pH of the second wash buffer is adjusted by using NaOH or KOH. In an embodiment, the pH of the second wash buffer is in the range between 9 and 11, preferably 10. Moreover, the volume of the second wash buffer is about 200 μl, but is not limited thereto.

An elution buffer is stored in the elution buffer chamber 14. The pH of the elution buffer is higher than 7 (e.g. 7~11). For example, the elution buffer includes but not limited to 2-amino-2-methyl-1-propanol (AMP), tris(hydroxymethyl)aminomethane (Tris), N,N,-bis-(2-Hydroxyethyl) glycine (BICINE) and 4-(2-hydroxyethyl)-1-piperazineethanesulfonic acid (HEPES). The pH of the elution buffer is adjusted by using NaOH or KOH. In an embodiment, the pH of the elution buffer is in the range between 9 and 11, preferably 9.5. Moreover, the volume of the elution buffer is about 150 μl, but is not limited thereto. Optionally, the elution buffer contains salts such as NaCl, KCl and/or NaF.

The chitosan coating material 150 is loaded in the nucleic acid catching chamber 15 for binding the nucleic acid and thus extracting the nucleic acid from the sample. In an embodiment, the chitosan coating material may be chitosan beads or a chitosan membrane, but not limited thereto. The chitosan coating material can be stably stored at room temperature to 56° C. for at least three months. Moreover, the waste liquid generated in the extraction process is collected in the waste chamber 16. After the extraction process is completed, the purified nucleic acid is collected in the nucleic acid collector 17.

Each chamber is connected to a piezoelectric micropump (not shown) through the pneumatic port of the chamber. Consequently, a pressurized gas can be introduced into each chamber. Moreover, the switch (not shown) at the inlet of each chamber is selectively turned on or turned off by an electromagnetic valve. Consequently, the pressurized gas will drive the fluids to flow between chambers of the biochip cartridge. The operating principles of the piezoelectric micropump and the electromagnetic valve are well known to those skilled in the art, and are not redundantly described herein.

Figure 2:
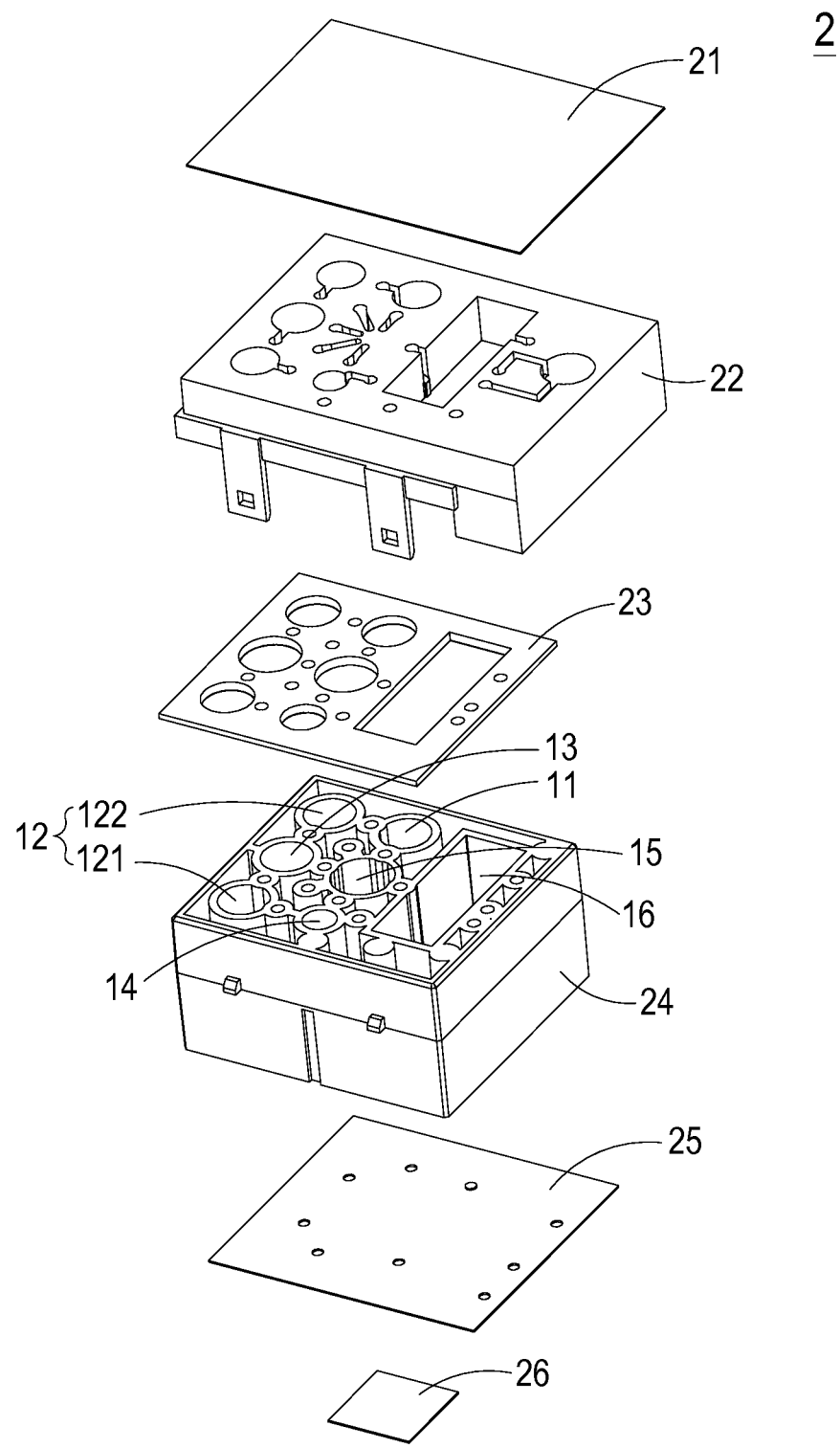
FIG. 2 is a schematic exploded view illustrating the structure of the biochip cartridge according to an embodiment of the present invention.
Figure 3:
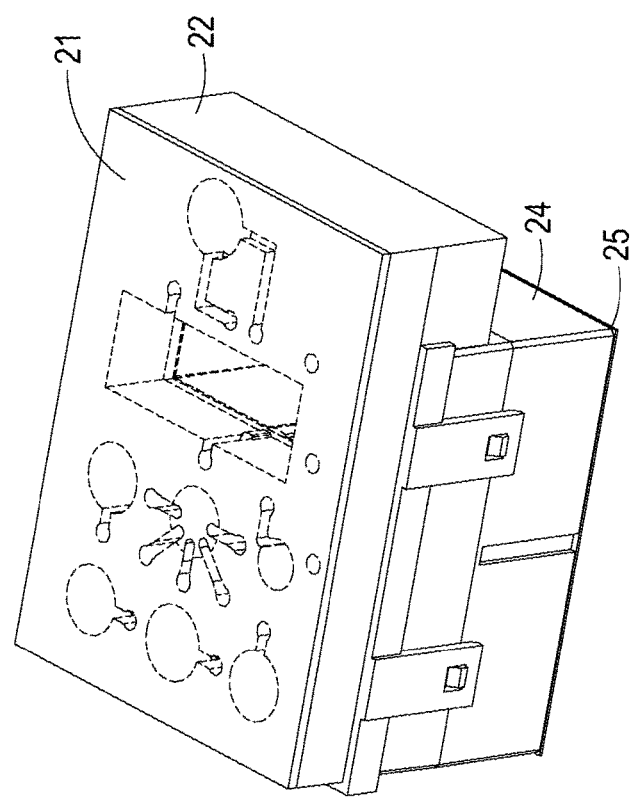
FIG. 3 is a schematic assembled view of the biochip cartridge of FIG. 2.

FIG. 2 is a schematic exploded view illustrating the structure of the biochip cartridge according to an embodiment of the present invention. FIG. 3 is a schematic assembled view of the biochip cartridge of FIG. 2. From top to bottom, the biochip cartridge 2 comprises a top plate 21, an upper cartridge part 22, a soft silicone part 23, a lower cartridge part 24, a bottom plate 25 and a heater plate 26. The top plate 21 is attached on the upper cartridge part 22. The bottom plate 25 is attached on the lower cartridge part 24. Consequently, a closed piping system of the biochip cartridge is established. Moreover, the upper cartridge part 22, the soft silicone part 23 and the lower cartridge part 24 are tightly engaged with each other, so that the sealing efficacy is enhanced. In some embodiments, a bottom side of the soft silicone part 23 has a raised ring structure (not shown). Due to the raised ring structure, the sealing efficacy of each chamber is enhanced after the upper cartridge part 22, the soft silicone part 23 and the lower cartridge part 24 are combined together.

The lower cartridge part 24 comprises the sample chamber 11, the first wash buffer chamber 12, the second wash buffer chamber 13, the elution buffer chamber 14, the nucleic acid catching chamber 15 and the waste chamber 16. These chambers have openings at the upper cartridge part 22. In addition, the nucleic acid collector 17 is connected to the upper cartridge part 22 as an external tube (not shown) and has an opening at the upper cartridge part 22. Consequently, the external tube containing the collected nucleic acid can be directly amplified or analyzed. An example of the external tube includes but is not limited to an eppendorf tube.

Moreover, the heater plate 26 is attached on the bottom plate 25 at the location corresponding to the nucleic acid catching chamber 15 in order to heat the nucleic acid catching chamber 15.

Figure 4:
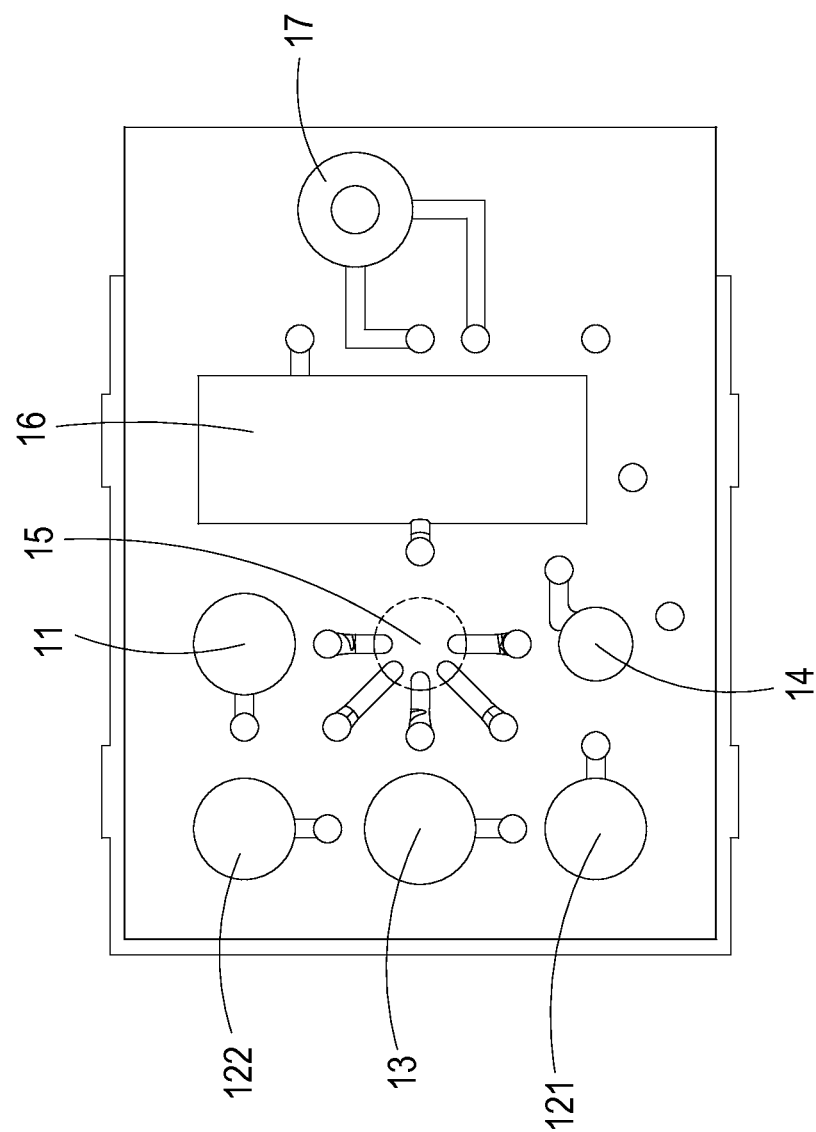
FIG. 4 is a schematic top view of the biochip cartridge of FIG. 2.

FIG. 4 is a schematic top view of the biochip cartridge of FIG. 2. For illustration, the top plate is not shown. In this embodiment, the first wash buffer chamber 12 comprises two sub-chambers 121 and 122. In another embodiment, the two sub-chambers 121 and 122 are replaced by a single chamber with larger capacity. In some other embodiments, the first wash buffer is continuously provided to achieve the similar washing function.

Figure 5:
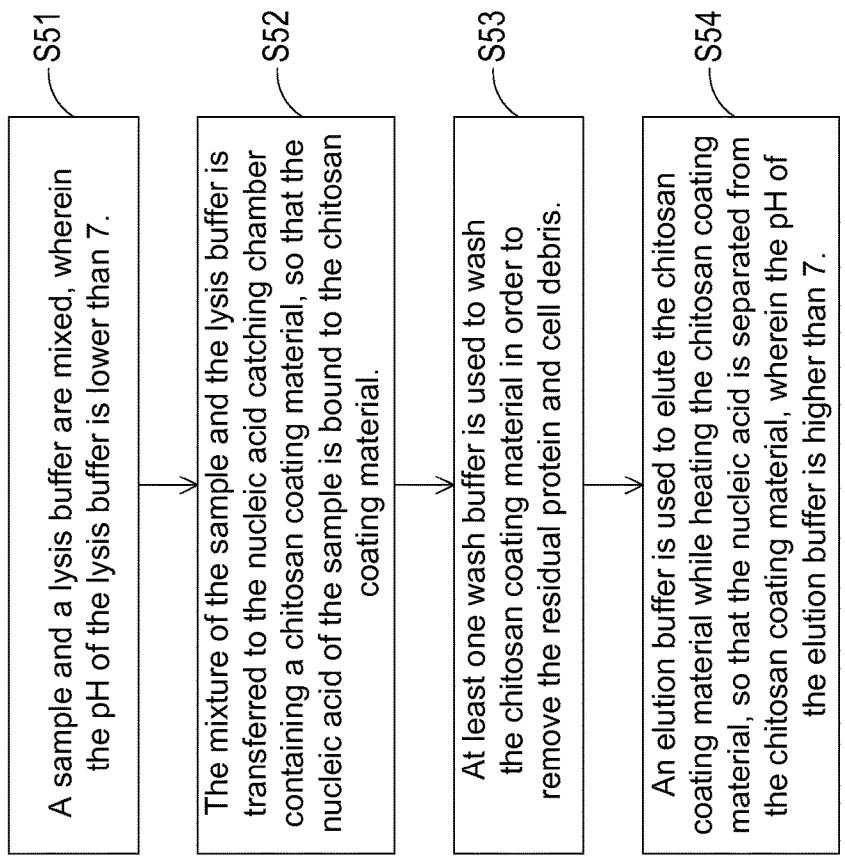
FIG. 5 is a flowchart illustrating the nucleic acid extraction method of the present invention.

Hereinafter, the nucleic acid extraction method of the present invention will be illustrated with reference to FIGS. 4 and 5. FIG. 5 is a flowchart illustrating the nucleic acid extraction method of the present invention.

Firstly, a sample and a lysis buffer are mixed, wherein the pH of the lysis buffer is lower than 7 (Step S51). Then, the mixture of the sample and the lysis buffer is transferred to the sample chamber 11 and incubated for a certain time period. Consequently, nucleic acid is released because of cell lysis. Then, the mixture of the sample and the lysis buffer is transferred to the nucleic acid catching chamber 15 containing a chitosan coating material, so that the nucleic acid of the sample is bound to the chitosan coating material (Step S52). In this step, a positive pressure is applied to the sample chamber 11 to push the mixture of the sample and the lysis buffer from the sample chamber 11 to the nucleic acid catching chamber 15. After a certain time period (e.g., 20-200 seconds), the nucleic acid of the sample is bound to the chitosan coating material. Then, the positive pressure is applied to the sample chamber 11 and a negative pressure is applied to the waste chamber 16. Consequently, the waste liquid is flushed out to the waste chamber 16.

Then, at least one wash buffer is used to wash the chitosan coating material in order to remove the residual protein and cell debris (Step S53). This step comprises two sub-steps S531 and S532. In the sub-step S531, the chitosan coating material is washed with a first wash buffer, wherein the pH of the first wash buffer is lower than 7. In the sub-step S532, the chitosan coating material is washed with a second wash buffer, wherein the pH of the second wash buffer is higher than 7.

In the sub-step S531, a positive pressure is applied to the sub-chamber 121 of the first wash buffer chamber 12 for a certain time period (e.g., 2-60 seconds). Consequently, the first wash buffer in the sub-chamber 121 of the first wash buffer chamber 12 is pushed to the nucleic acid catching chamber 15. Then, the positive pressure is applied to the sub-chamber 121 of the first wash buffer chamber 12 and a negative pressure is applied to the waste chamber 16 for a certain time period (e.g., 2-60 seconds). That is, the first wash buffer is continuously transferred from the sub-chamber 121 of the first wash buffer chamber 12 to the waste chamber 16 through the nucleic acid catching chamber 15. Consequently, the residual protein and the cell debris are removed.

For increasing the washing efficacy, the sub-step S531 is performed twice. That is, the first wash buffer in the sub-chamber 122 of the first wash buffer chamber 12 is used to wash the chitosan coating material again. In particular, a positive pressure is applied to the sub-chamber 122 of the first wash buffer chamber 12 for a certain time period (e.g., 2-60 seconds). Consequently, the first wash buffer in the sub-chamber 122 of the first wash buffer chamber 12 is pushed to the nucleic acid catching chamber 15. Then, the positive pressure is applied to the sub-chamber 122 of the first wash buffer chamber 12 and a negative pressure is applied to the waste chamber 16 for a certain time period (e.g., 2-60 seconds). That is, the first wash buffer is continuously transferred from the sub-chamber 122 of the first wash buffer chamber 12 to the waste chamber 16 through the nucleic acid catching chamber 15. Consequently, the residual protein and the cell debris are removed.

In the sub-step S532, the chitosan coating material is washed with the second wash buffer, wherein the pH of the second wash buffer is higher than 7. By applying a positive pressure to the second wash buffer chamber 13 and applying a negative pressure to the waste chamber 16, the second wash buffer is continuously transferred from the second wash buffer chamber 13 to the waste chamber 16 through the nucleic acid catching chamber 15. Consequently, the residual protein and the cell debris are removed. Moreover, since the pH of the second wash buffer is higher than 7, the pH of the nucleic acid catching chamber 15 is close to 7.

Then, in a step S54, an elution buffer is used to elute the chitosan coating material while heating chitosan coating material. Consequently, the nucleic acid is separated from the chitosan coating material, wherein the pH of the elution buffer is higher than 7. By applying a positive pressure to the elution buffer chamber 14, the elution buffer in the elution buffer chamber 14 is pushed to the nucleic acid catching chamber 15 and incubated for about 10~15 minutes. At the same time, the heater plate 26 under the nucleic acid catching chamber 15 performs heating to the chitosan coating material in the nucleic acid catching chamber 15 to 35~65° C., for example 45-55° C. and preferably 50° C.

Consequently, the nucleic acid is separated from the chitosan coating material. Then, by applying a positive pressure to the elution buffer chamber 14 and applying a negative pressure to the nucleic acid collector 17, the elution buffer contains the nucleic acid is pushed to the nucleic acid collector 17.

In this embodiment, since the pH of the nucleic acid catching chamber 15 is increased to about 7, it is not necessary to neutralize the pH in the eluting step. Under this circumstance, the eluting efficiency is not deteriorated. Moreover, since the eluting step and the heating step are simultaneously performed, the eluting efficiency is enhanced, and since the eluting efficiency is enhanced, the yield and purity of the nucleic acid are both increased.

Certainly, the reaction time, volume, pH and other operating conditions of the above steps may be adjusted according to the practical requirements.

Figure 6B:
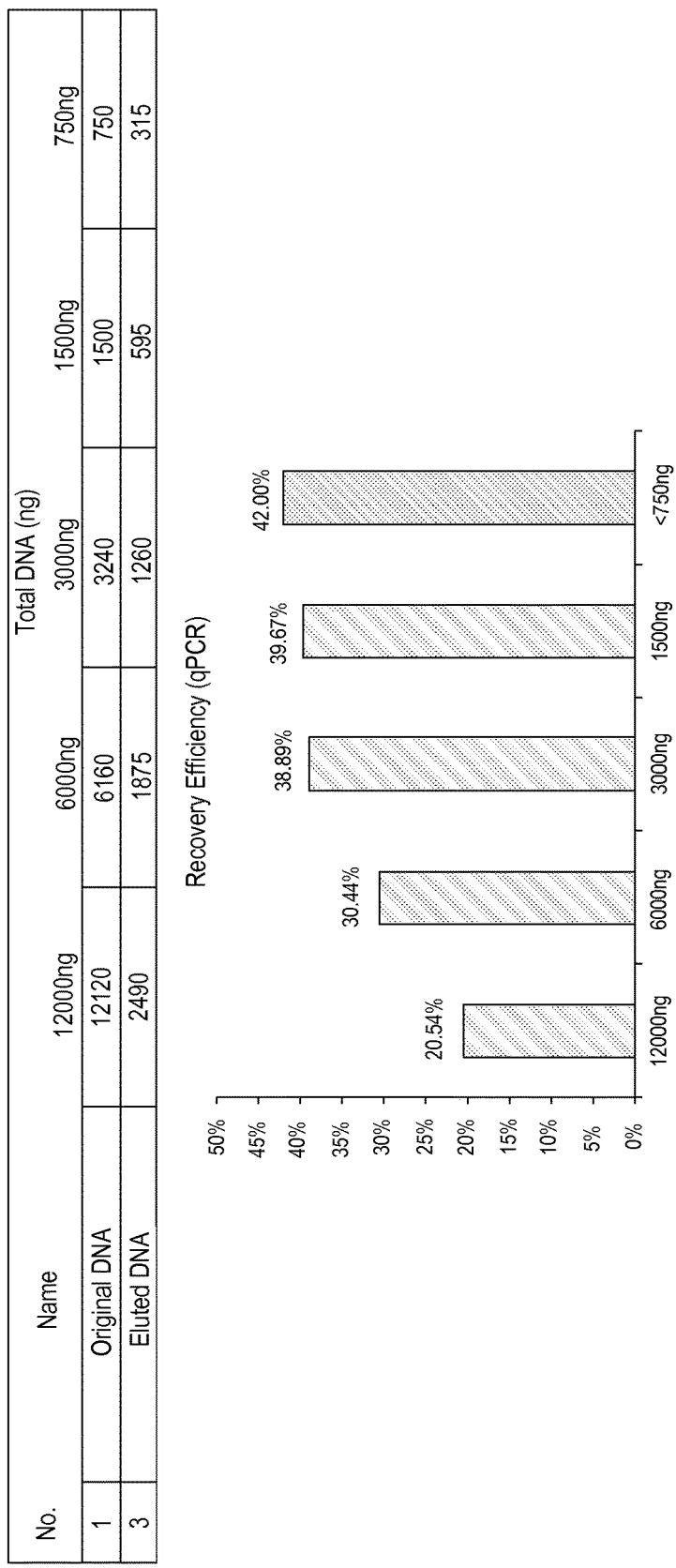

FIGS. 6A and 6B illustrate the DNA extraction results of the rat genomic DNA by the nucleic acid extraction method of the present invention. In FIG. 6A, 3000 ng of rat genomic DNA is extracted by the nucleic acid extraction method of the present invention. The recovery is about 40%. As known, if the 260/280 ratio (i.e., the ratio of nucleic acid to protein) and the 260/230 ratio (i.e., the ratio of nucleic acid to organic compounds) are both in the range between 1.8 and 2.0, it means that the purity and the quality of the nucleic acid are satisfactory. As shown in FIG. 6A, the 260/280 ratio and the 260/230 ratio for the extracted DNA according to the method of the present invention lies in or is close to 1.8~2.0. In other words, the purity and the quality of the nucleic acid extracted by the method of the present invention are satisfactory.

FIG. 6B shows the linear effect of the nucleic acid extraction method of the present invention. In this experiment, 90~12000 ng of rat genomic DNA is extracted by the nucleic acid extraction method of the present invention. The result of the quantitative analysis by NanoDrop Spectrophotometer and qPCR indicates that the recovery of the sample with lower than 3000 ng of DNA is also close to 40%. That is, the linear effect is very good. Moreover, the recovery of the sample with 6000 ng of DNA is 30.44%, and the recovery of the sample with 12000 ng of DNA is only 20.54%. The low recovery hints that the extractable amount of DNA exceeds the maximum capacity of the chitosan coating material. That is, the maximum capacity of the chitosan coating material is at around 3000~6000 ng of DNA. Moreover, since the nucleic acid extraction method of the present invention can extract 90 ng or less of DNA, the nucleic acid extraction method of the present invention can be applied to trace extraction and detection. In other words, the nucleic acid extraction method of the present invention can extract 90-6000 ng of DNA, which means the extractable range of the nucleic acid extraction method provided in the present invention is very wide.

Figure 7:
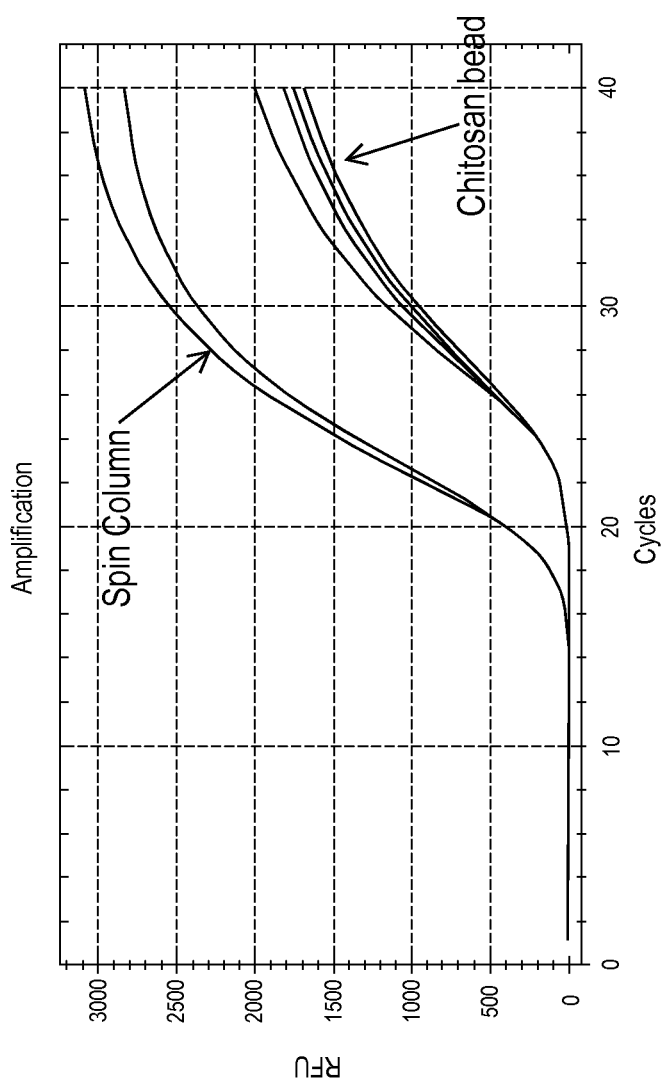
FIG. 7 illustrates the DNA extraction result of the human cell DNA by using the nucleic acid extraction method of the present invention.

FIG. 7 illustrates the DNA extraction result of the human cell DNA by using the nucleic acid extraction method of the present invention. Human cells (HCT116 cell line) are extracted by the nucleic acid extraction method of the present invention and a commercially available spin column extraction kit, and the quantitative analysis is made by using qPCR. The experiment results show that the recovery of the nucleic acid extraction method of the present invention is lower than the recovery of the commercially available spin column extraction kit. However, the nucleic acid extraction method of the present invention is capable of extracting DNA from the human cells.

From the above results of the experiments, the nucleic acid extraction method of the present invention can effectively extract the nucleic acid from the sample at a recovery of 40% and at the maximum extractable amount of 3000 ng. In comparison with the conventional extraction method using chitosan coating material, the nucleic acid extraction method of the present invention has higher extractable capacity and better linear effect and is suitable for quantitative analysis. Moreover, the nucleic acid extraction method of the present invention can be applied to trace extraction and detection.

From the above descriptions, the present invention provides an improved nucleic acid extraction method. In accordance with the present invention, chitosan coating material is used to extract nucleic acid. Since the inhibitory chemicals (e.g., guanidium hydrochloride, ethanol and isopropanol) are not contained in the buffer system, the yield of the high purity nucleic acid is increased and the result of the subsequent DNA analysis is not adversely affected. Moreover, since the pH is increased to about 7 by using the second wash buffer, it is not necessary to neutralize the pH in the eluting step. Moreover, since the eluting step and the heating step are simultaneously performed, the eluting efficiency is enhanced and the yield and purity of the nucleic acid are both increased. Moreover, since the nucleic acid extraction method of the present invention is applied to a biochip cartridge and adopts a microfluidic control technology, the DNA of the sample can be automatically extracted and purified. Consequently, the technology of the present invention can be used in rapid clinical diagnosis and accurate screening. In other words, the technology of the present invention has the potential for commercialization, and can improve the diagnosis of infectious diseases and provide immediate in-situ detection.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A nucleic acid extraction method implemented in a biochip cartridge having a sample chamber, a first wash buffer chamber, a second wash buffer chamber, an elution buffer chamber, a nucleic acid catching chamber and a waste chamber, wherein the nucleic acid catching chamber is connected with all the other chambers, and a pressurized gas is introduced into the chambers to drive fluids to flow between the chambers of the biochip cartridge, the nucleic acid extraction method comprising steps of:

(a) providing a mixture of a sample and a lysis buffer in the sample chamber, wherein the pH of the lysis buffer is lower than 7;

(b) transferring the mixture of the sample and the lysis buffer to a nucleic acid catching chamber containing chitosan beads or chitosan membrane by applying a positive pressure to the sample chamber, so that nucleic acid of the sample is bound to the chitosan beads or chitosan membrane;

(c) pushing a first wash buffer having a pH lower than 7 from the first wash buffer chamber to the nucleic acid catching chamber by applying a positive pressure to the first wash buffer chamber for a certain time period, and then washing the chitosan beads or chitosan membrane with the first wash buffer from the first wash buffer chamber by applying a positive pressure to the first wash buffer chamber and applying a negative pressure to the waste chamber, so that the first wash buffer is continuously transferred from the first wash buffer chamber to the waste chamber through the nucleic acid catching chamber to remove residual protein and cell debris;

(d) neutralizing the pH of the nucleic acid catching chamber through washing the chitosan beads or chitosan membrane with a second wash buffer from the second wash buffer chamber by applying a positive pressure to the second wash buffer chamber and applying a negative pressure to the waste chamber, so that the second wash buffer is continuously transferred from the second wash buffer chamber to the waste chamber through the nucleic acid catching chamber, wherein the pH of the second wash buffer is in a range between 9 and 11 to increase the pH of the nucleic acid catching chamber to close to 7; and (e) eluting the chitosan beads or chitosan membrane with an elution buffer from the elution buffer chamber by applying a positive pressure to the elution buffer chamber while heating the chitosan beads or chitosan membrane, so that the nucleic acid is separated from the chitosan beads or chitosan membrane, wherein the pH of the elution buffer is in a range between 9 and 11, wherein the step (c) is performed twice for increasing washing efficacy.

2. The nucleic acid extraction method according to claim 1, wherein the pH of the first wash buffer is in a range between 4 and 7.

3. The nucleic acid extraction method according to claim 1, wherein the first wash buffer includes tris(hydroxymethyl) aminomethane (Tris), bis(2-hydroxyethyl)amino tris(hydroxymethyl)methane (BIS-TRIS), 1,3-bis(tris(hydroxymethyl)methylamino) propane (Bis-Tris Propane) and 3-(N-morpholino)propanesulfonic acid (MOPS).

4. The nucleic acid extraction method according to claim 1, wherein the second wash buffer includes 2-amino-2-methyl-1-propanol (AMP), tris(hydroxymethyl)aminomethane (Tris), N,N,-bis-(2-Hydroxyethyl) glycine (BICINE) and 4-(2-hydroxyethyl)-1-piperazineethanesulfonic acid (HEPES).

5. The nucleic acid extraction method according to claim 1, wherein the pH of the lysis buffer is in a range between 4 and 7.

6. The nucleic acid extraction method according to claim 1, wherein the lysis buffer includes tris(hydroxymethyl) aminomethane (Tris), bis(2-hydroxyethyl)amino tris(hydroxymethyl)methane (BIS-TRIS), 1,3-bis(tris(hydroxymethyl)methylamino) propane (Bis-Tris Propane) and 3-(N-morpholino)propanesulfonic acid (MOPS).

7. The nucleic acid extraction method according to claim 1, wherein the lysis buffer contains a cell lysis detergent.

8. The nucleic acid extraction method according to claim 1, wherein the elution buffer includes 2-amino-2-methyl-1-propanol (AMP), tris(hydroxymethyl)aminomethane (Tris), N,N,-bis-(2-Hydroxyethyl) glycine (BICINE) and 4-(2-hydroxyethyl)-1-piperazineethanesulfonic acid (HEPES).

9. The nucleic acid extraction method according to claim 1, wherein in the step (d), the chitosan beads or chitosan membrane is heated to 35~65° C.

10. The nucleic acid extraction method according to claim 1, wherein a heater plate is disposed under the nucleic acid catching chamber for heating the chitosan beads or chitosan membrane.

* * * * *